United States Patent
Kolzau et al.

(10) Patent No.: US 7,153,433 B2
(45) Date of Patent: Dec. 26, 2006

(54) USE OF FUNCTIONALIZED POROUS MEMBRANES OR MATRICES FOR PURIFICATION OF NUCLEIC ACIDS AND CORRESPONDING METHODS

(75) Inventors: Thomas Kolzau, Hamburg (DE); Heinz Gerhard Köhn, Hamburg (DE); Wilhelm Plüster, Hamburg (DE); Mathias Ulbricht, Berlin (DE)

(73) Assignee: Eppendorf AG, Hamburg (DE)

( * ) Notice: Subject to any disclaimer, the term of this patent is extended or adjusted under 35 U.S.C. 154(b) by 579 days.

(21) Appl. No.: 10/182,852

(22) PCT Filed: Feb. 2, 2001

(86) PCT No.: PCT/EP01/01133

§ 371 (c)(1),
(2), (4) Date: Aug. 2, 2002

(87) PCT Pub. No.: WO01/59097

PCT Pub. Date: Aug. 16, 2001

(65) Prior Publication Data

US 2003/0191302 A1  Oct. 9, 2003

(30) Foreign Application Priority Data

Feb. 11, 2000 (DE) .................. 100 06 590

(51) Int. Cl.
- *B01D 61/00* (2006.01)
- *C07H 19/04* (2006.01)
- *C12Q 1/68* (2006.01)
- *B01D 63/00* (2006.01)

(52) U.S. Cl. .......... 210/651; 536/25.4; 536/25.6; 435/6; 435/483; 435/490; 435/299.1

(58) Field of Classification Search ........ 210/645, 210/500.27, 656, 660, 638, 198, 500.35, 210/651; 422/101; 435/13, 6, 7.2, 7.21, 435/7.32, 270, 483, 490, 297.1, 299.1, 180, 435/181; 536/25.4, 25.6; 521/25

See application file for complete search history.

(56) References Cited

U.S. PATENT DOCUMENTS

| | | | | |
|---|---|---|---|---|
| 4,113,912 A | * | 9/1978 | Okita | 442/118 |
| 4,794,088 A | * | 12/1988 | Miyaki et al. | 436/161 |
| 4,814,372 A | * | 3/1989 | Caporiccio et al. | 528/485 |
| 5,438,128 A | * | 8/1995 | Nieuwkerk et al. | 536/25.4 |
| 5,599,667 A | * | 2/1997 | Arnold et al. | 435/6 |
| 5,674,997 A | * | 10/1997 | Woodard et al. | 536/25.4 |
| 5,693,785 A | | 12/1997 | Woodard et al. | |

(Continued)

FOREIGN PATENT DOCUMENTS

WO WO 99/29703 * 6/1999

OTHER PUBLICATIONS

Ulbricht M et al: "Ultrafiltration membrane surfaces with grafted polymer 'tentacles': preparation, characterization and application for covalent protein binding", Biomaterials, GB Elsevier Science Publishers, vol. 19, No. 14, Jul. 1998.

*Primary Examiner*—Ana Fortuna
(74) *Attorney, Agent, or Firm*—Rankin, Hill, Porter & Clark LLP

(57) ABSTRACT

Application of a functionalized porous membrane to purify nucleic acids, the binding properties of the membrane with respect to nucleic acids being adjustable by controlling the conditions of an ambient medium. The membrane is functionalized by deprotonated groups.

16 Claims, 1 Drawing Sheet

Gel-electrophoretic analysis after purifying the GFP-N1 plasmid (Clontech)

U.S. PATENT DOCUMENTS 6,120,985 A * 9/2000 Laugharn et al. ............ 435/1.3
6,258,057 B1 * 7/2001 Marinello et al. ............ 604/77
6,413,621 B1 * 7/2002 Mayes et al. ................ 428/212
6,524,482 B1 * 2/2003 Bruening et al. ........... 210/651
6,783,937 B1 * 8/2004 Hou et al. ..................... 435/6
6,860,393 B1 * 3/2005 Hou et al. ................... 210/435
6,914,137 B1 * 7/2005 Baker ........................ 536/25.4
2003/0078314 A1 * 4/2003 Travis et al.
2004/0209258 A1 * 10/2004 Parthasarathy et al.

* cited by examiner

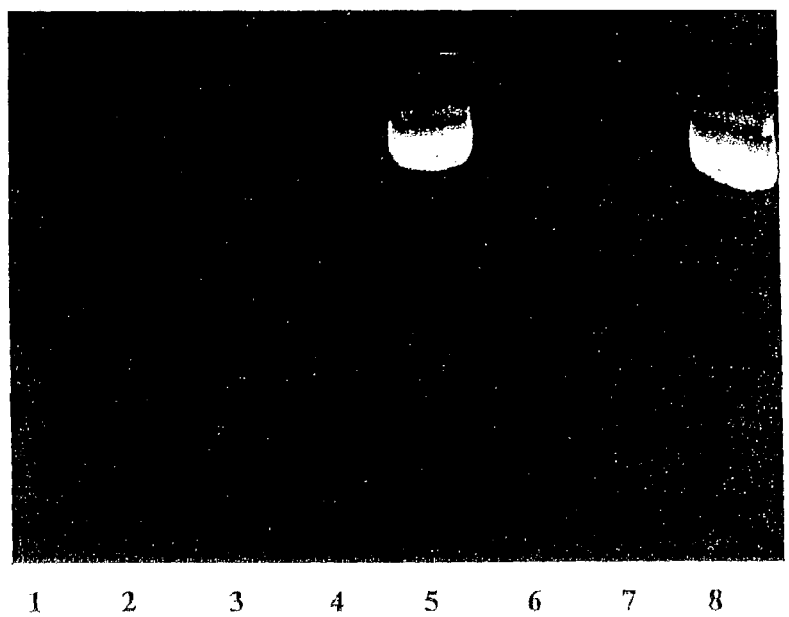
Fig. 1: Gel-electropheretic analysis after purifying the GFP-N1 plasmid (Clontech)

USE OF FUNCTIONALIZED POROUS MEMBRANES OR MATRICES FOR PURIFICATION OF NUCLEIC ACIDS AND CORRESPONDING METHODS

BACKGROUND OF THE INVENTION

1. Field of the Invention

The present invention relates generally to a functionalized membrane and a matrix to purify nucleic acids, and particularly to a method for purifying the nucleic acids by means of such membranes and matrices.

2. Discussion of Related Art

Membranes useful to purify nucleic acids are commonly known from, for example, U.S. Pat. No. 5,438,128. The membranes are typically a porous polymer made of polypropylene or nylon, and are functionalized with ion-exchange groups. At low ion concentrations, the functionalized membranes bind to ionized nucleic acids, and at high ion concentrations the bound nucleic acids are eluted.

The known porous membranes are used in methods or kits to purify nucleic acids. In general, the raw material containing the nucleic acids, which may have to be pre-purified, is in a low ionic-concentration binding buffer solution and is aspirated or pressed through the membrane. When moving through the membrane, the nucleic acids are selectively bound by the ion-exchange groups to the membrane surface. In a subsequent step, the membrane is washed to separate non-specifically bound contaminants. Optionally, the wash is accomplished using a buffer of higher ionic strength. The elution of the bound nucleic acids then takes place in a further stage using a buffer of still higher ionic strength.

A feature of the membranes of the present invention is that the membranes that are useful to purify nucleic acids have surfaces that are functionalized with deprotonatable groups. Such membranes are described by ULBRICHT & RIEDEL in BIOMATERIALS 19 (1998), pp 1,229–1,237 only in conjunction with protein immobilization. A goal of the invention, namely purifying nucleic acids, was not mentioned or implied by the reference.

Unfortunately, because of the high salt concentration the eluate must be purified in almost all cases before it may be processed further. The purification step uses, for example, ethanol precipitation or dialysis.

As disclosed in U.S. Pat. No. 5,693,785, hydroxylated silica beads are sometimes used to purify nucleic acids. When the beads are used, a chaotropic buffer is required to assure adequate binding of the DNA to the silica beads. In the absence of chaotropic binding buffers, binding takes place only when the surface is strongly positively charged.

SUMMARY OF THE INVENTION

The present invention provides a membrane and a matrix to purify nucleic acids. The binding properties of the membrane and matrix, as they relate to nucleic acids, can be controlled to create a nucleic-acid purification method which is matched to the membrane and the matrix.

An aspect of the membrane of the invention is that, because of the functionalization with deprotonatable groups, the membrane exhibits a controllable (switchable) adjustable affinity for nucleic acids. The membrane binding properties can be reproducibly adjusted in, for example, a pH-dependent manner and/or in relation to ion concentration.

BRIEF DESCRIPTION OF THE DRAWINGS

These and further features of the invention will be apparent with reference to the following description and drawings, wherein:

FIG. 1 is a graph of a gel-electrophoresis after purifying a GFP-N1 plasmid (Clontech).

DETAILED DESCRIPTION OF PREFERRED EMBODIMENTS

The present invention provides a membrane that can be used to purify nucleic acids. Exemplary nucleic acids include PCR batches, mRNA, total RNA and DNA, and preferably plasmid DNA (pDNA) and genomic DNA. In another aspect of the invention, a matrix is used rather than the membrane. The purification process can be accomplished by controlling the pH and/or the ion concentration of a solution containing the nucleic acids.

In a first embodiment, the membrane is formed of plastic. Preferred plastic materials are polypropylene, polyamides, polyesters, polysulfone, polyvinylidene fluoride (PVDF) and combinations thereof. In alternative embodiments, the membrane is formed of an inorganic material, for example, aluminum oxide, titanium oxide, zirconium oxide and silicon dioxide.

The membrane in a solid phase is in sheet-form, preferably with a thickness of less than about 500 microns ($\mu$) and has a pore diameter in a range of between about 0.2 and about 10$\mu$.

For pH values less than or about the same as the pK values of the surfaces and/or at raised ionic concentrations, the membrane exhibits good nucleic-acid binding properties. If the pH is shifted toward the alkaline side, and/or the ionic concentration of the ambient medium of the membrane is lowered, then the membrane's affinity for nucleic acids is reduced. Under such conditions, the bound nucleic acids can be eluted. As a result, the conditions under which the membranes may be used for nucleic-acid purification therefore may be selected in a highly diverse manner and can be matched to various applications.

The membrane of the first embodiment is functionalization to exhibit hydrophilic surface properties and therefore has good wetting properties. Because of the good wetting properties of the surface, elution buffer volumes may be kept relatively small.

Groups of sulfonic acid, carboxylic acid and phosphoric acid functionalize the membrane. The functional membrane exhibits especially rigorously switchable surface properties. That is, the affinity for nucleic acids can be well and narrowly controlled by means of the pH value and/or the ionic concentration of the ambient medium.

In an alternative embodiment, the switchable surface properties of the membrane can be constituted directly by configuring the protonatable groups at or in the membrane surface. A factor in this respect is that the groups come into contact with the ambient medium and, depending on conditions in the medium, are in a neutral or deprotonated state.

When using a functionalized membrane in accordance with the invention, the nucleic acids are preferably bound in the absence of chaotropic reagents. The elution of the bound nucleic acids is feasible at low-salt conditions and under some conditions at room temperature, whereby processing is substantially simplified. Still, if so desired, processing in the presence of chaotropic reagents also is possible.

In a second embodiment, protonatable groups are, present on a polymer chain, for example, a polyacrylic acid polymer chain. One end of the polymer chain is fixed to the membrane surface and the other end is freely displaceable.

The membrane with protonatable groups on polymer chains can assume various boundary conditions. At a pH value less than the order of the pK value of the membrane surface, i.e. at higher ionic concentrations (for instance>500 mM), the polymer chains rest tightly against the membrane. In this state, the nucleic-acid molecules may be efficiently adsorbed to the membrane surface. Pertinent factors include heterogeneous interactions, for example, Van der Waals forces and hydrophobic and ionic interactions between the nucleic acid and the polymer chain, and also the functional groups of the polymer chain.

If the environment of the membrane is adjusted to a neutral-to-alkaline pH value and/or to a low ionic concentration, the polymer chains are biased away from the membrane surface. In this state, the bound nucleic acids may be eluted from the polymer chains. Both ionic interactions (the functional groups in the polymer chains are negatively charged and repel the nucleic-acid molecule, which is, also negatively charged) and mechanical factors may be involved.

The membrane according to the second embodiment is particularly useful in a high-flow application. Alternative embodiments are particularly useful in micro-titration filter trays, spin columns and reaction containers.

In a third embodiment, a permeable matrix is used for separating nucleic acids. The matrix of this embodiment has a functionalized surface similar to the functionalized surface of the membrane of the first embodiment discussed above.

A preferred matrix could be shaped as a filter. In alternative embodiments, other shapes, for example, non-woven webs, felt, fibers and sintered materials may also be used. In yet other alternative embodiments, a designed pipette tip and a reaction container (consumables) may be used. The pipette tip and the reaction container can be fitted with microstructured ducts.

With reference to the method for nucleic-acid purification using a membrane and a matrix in accordance with the invention, nucleic acids can be bound in a selective manner, if desired. Non-selective binding can also be accomplished, for example, with a flow-crossed matrix.

In a first method in accordance with the invention, nucleic acid binding is attained by letting a solution of the raw material containing the nucleic acids to permeate and flow through the membrane a binding buffer is used. The binding buffer preferably has an ionic concentration exceeding 100 mM, the pH value being adjusted to be less or about that of the pK value of the membrane or matrix surface. Reproducible quantitative yields are observed at such values. During such a flow, the nucleic acids are selectively absorbed by the membrane surface. In an especially preferred method, the ionic concentration of the binding buffer is adjusted to be >500 mM.

In a second method, the affinity of the membrane/matrix to nucleic acids may be adjusted by means of the pH value. In this method, a binding buffer is selected with a pH such as to be about the same as, or less than, the pK value of the membrane surface. Under these conditions, the nucleic acids are absorbed nearly quantitatively when a solution of the raw material containing the nucleic acids is allowed to permeate the membrane into a binding powder of the cited pH value.

In a third method, the raw material is placed into a binding buffer containing a precipitant of a concentration less than the value at which nucleic acids are precipitated. Preferably, polyethyleneglycol (PEG) is added to the binding buffer at about 6% concentration. In particular, PEG 8000, commercially available from Alfa Aesar Corporation (Ward Hill, Mass.) is preferred. In this example, the nucleic acids bind about quantitatively onto the membrane surface.

In the above three exemplary methods, adsorption will take place only after the membranes have been correspondingly functionalized. No binding, or no significant binding, takes place on unfunctionalized membranes. This behavior is attributed to the cited ambient conditions favoring nucleic-acid binding independently from one of another and only in conjunction with the special membrane surface.

The individual parameters also may be linked to one another, that is, the membrane designed to bind nucleic acids can be adjusted to an ambient medium of high ionic concentration and low pH value. The binding buffer may be provided separately. But, the binding buffer can be combined with at least one lysing buffer.

With reference to the above described methods, the bound nucleic acids can also be eluted from the membrane, possibly following a washing step. The methods that bound the nucleic acids to the membranes can be reversed so as to elute the bound nucleic acids.

The elution is carried out with water at a neutral pH value. When in the presence of water, the functional groups of the membrane are deprotonated in large part. The charges, as well as the membrane and the nucleic acids, are not shielded. Ionic repulsive motions take place that can detach the nucleic acids from the membrane. If the membrane or matrix contains polymer chains where the functional groups are configured, like the third embodiment discussed above, another effect is added. The free ends of the chains point away from the membrane and—in addition to the above described ionic interactions—repel the nucleic acids in a purely mechanical manner.

In addition to pure water, other elution buffers are also useful. An appropriate elution buffer is readily ascertainable to one skilled in the art without undue experimentation. Preferably, the ionic concentration of the elution buffer should be as low as possible and the pH value should be adjusted to be as much above the pK value of the membrane surface as possible. A higher ionic concentration of the elution buffer may be compensated for by a more alkaline pH value, and vice versa. Both values can be readily optimized.

The application of functionalized membranes and matrices, and the corresponding methods allow for efficient purification of nucleic acids employing conventional stages. The convention stages include binding the nucleic acids to a membrane, washing the membrane and eluting the bound nucleic acids. The stages can be carried out in a conventional manner, under gentle conditions and at good yields.

The typically required chaotropic reagents and the conventionally employed beads may be eliminated by practicing the invention. Also, because the membranes and matrices of the present invention exhibiting good wetting properties, the elution may be carried out with minimal buffer volumes, and at room temperature, if desired.

The invention is particularly applicable to processing plasmid DNA for sequencing—a preferred field of application. Naturally, other nucleic acids may be purified—where called for following pre-purification from the most diverse raw materials containing such nucleic acids.

EXAMPLES

The invention is elucidated below in relation to several Examples which concern especially preferred implementations.

Example 1

Preparing Functionalized Membranes

A) Modifying Polypropylene (PP) Membranes.

Sample 1) A polypropylene microfiltration membrane was equilibrated with a 100 micromolar (mM) solution of benzophenone (BP) in acetone by immersing the membrane in the solution and agitating for 2 hours. The polypropylene microfiltration membrane was an Accurel 2E HF, with a nominal pore size of 0.2μ and a membrane thickness of 150μ, commercially available from Membrana GmbH (Wuppertal, Germany) or a test specimen #1333-12A, with a nominal pore size of 0.45μ and a membrane thickness of 110μ, commercially available from 3M corporation (St. Paul, USA) having a diameter (d)=80 millimeters (mm).

Next, the membrane was coated with a 10% aqueous acrylic-acid solution. The coated membrane was illuminated for 15 minutes with ultraviolet (UV) radiation from a UVA-Spot 2000, commercially available from Dr Hönle GmbH (Planegg, Germany). Finally the modified membrane was extracted with water for 24 hours at 60° Celsius and then dried.

Sample 1 was surface-modified PP (Example 1) having a nominal pore width of 0.45μ. A 3,000 rotations per minute (rpm) centrifuge, for example an Eppendorf 5810R, A-2 DPW rotor, commercially available from Brinkmann Instruments, Inc. (Westbury, N.Y.), was used to purify sample 1, at room temperature, using the bind/wash/elute principle.

B) Modifying Nylon Membranes

Sample 2) A nylon microfiltration membrane, for example a nylon membrane commercially available from Schleicher & Schüll, Inc. (Keene, N.H.), with a nominal pore size of 0.45μ and a membrane thickness 127μ was modified under the same conditions as in Example 1, above.

B: Purifying Nucleic Acids

Samples 1 and 2 were clamped into a 96-microfiltration tray during the following purification procedures.

Procedure 1:

1 μg of pDNA was added each iteration to the particular 200 μltr of binding buffer 1 (BB1) or 2 (BB2) (BB1: 5 mM tris, pH=7.5; BB2: 4 M NaCl, pH=4.6). Following incubation, washing was carried out twice. Each wash was done with 200 μltr of 70% ethanol (EtOH). Elution was carried out with 30 μltr tris (5 mM, pH=7.5). Lastly a second elution with 100 μltr was carried out. Semi-quantitative analysis of 4 μltr eluate was carried out using ethidium bromide gel electrophoresis.

Because adsorption to the membrane does not take place when using the binding buffer BB1, plasmid DNA (pDNA) when using BB2 may be bound nearly quantitatively to the membrane and may be eluted again in the first elution stage.

With reference to Table 1, a test was carried out in the manner similar to that described in relation to Procedure 1; the binding buffers listed in Table 1 were used. The amount of pDNA used was 500 ng. Semi-quantitative analysis was carried out by means of gel electrophoresis (test results not shown). Analysis is shown (in Table 1) and allows a first estimate of the recovery rate (from − to +++).

TABLE 1

| Binding buffer | nylon, 0.45μ (S&S), unmodified | PP, 0.45μ, hydrophilic, GH Polypro (Pall Co.) | PP, 0.45μ modified with acrylic acid |
|---|---|---|---|
| pH = 3.5, 1.5 M NaCl | (+) | − | +++ |
| pH = 7.4, 1.5 M NaCl | (+) | − | − |

As shown in Table 1, the DNA was bound in a nearly quantitative manner and then was eluted again only as regards the acrylic-acid modified PP membrane. Table 1 illustrates the binding dependency on the pH value of the incubation solution. Binding takes place at a pH value less than the pK value of the membrane modification. No binding takes place at a pH value larger than the pK value.

Example 2

Alkaline Lysing

Plasmid DNA (pDNA) purification was carried out on the principle of alkaline lysing as generally known to one skilled in the art. For that purpose, 1.5 ml of bacterial culture was mixed with the buffers B1–B3 (B1=100 μltr; B2=300 μltr; B3=300 μltr) from the Eppendorf "Perfect Prep Plasmid Midi" kit, commercially available from Brinkmann Instruments, Inc. (Westbury, N.Y.). Following centrifuging, the clear lysate was mixed each time with 700 μltr of binding buffer (see Table 2). The specimen was processed under the conditions listed in Example 1.

The control was in the form of a plasmid preparation, the full purification procedure being carried out with the "Perfect Prep Plasmid Mini" kit from the identical 1.5 ml of bacterial culture. As a further control, the mixture of clear lysate and the particular binding buffer (Table 2) was centrifuged at room temperature for 30 minutes at 12,000 rpm. The supernatant was removed. Thereupon, the sample was washed twice with 200 μltr of 70% ethanol. And, drying was under vacuum with the addition of 30 μltr tris-HCl, pH=7.5.

The yield and the purity were determined by photometry and analysis by ethidium bromide gel electrophoresis (Table 2, FIG. 1). Table 2 lists the concentration of the eluted pDNA in ng/μltr ascertained using a photometer (for example, an Eppendorf biophotometer).

TABLE 2

| | Binding buffer: 6% PEG (mol. wt. = 8,000) pH = 4.6 | Binding buffer: 6% PEG (mol. wt. = 8,000) pH = 7.4 |
|---|---|---|
| Nylon, 0.45μ, unmodified (S&S) | 8 ng/μltr | 15 ng/μltr |
| Nylon, 0.45μ coated with acrylic acid | 80 ng/μltr | 16 ng/μltr |

The plasmid DNA of the GFP-N1 was analyzed following separation in 0.8% ethidium bromide agarose gel as shown in FIG. 1. The control was the plasmid mini preparation (Eppendorf Perfect Prep Mini).

The tracks of the gel shown in FIG. 1 were loaded as follows:
1) control (without membrane) to show a precipitation mechanism, pH of binding buffer=7.4, i.e., the plamid mini preparation;
2) control (without membrane) to show a precipitation mechanism, pH of binding buffer=4.6;
3) unmodified membrane, pH of binding buffer=4.6;
4) unmodified membrane, pH of binding buffer=7.4;
5) modified membrane, pH of binding buffer=4.6;
6) modified membrane, pH of binding buffer=7.4; and
7) empty.

The Gel of FIG. 1 illustrates that the pDNA may only be purified when using the modified nylon membrane. Purification depends on the selected pH value. Thus, successful pDNA isolation could be carried out only upon using the binding buffer at pH=4.6, and not when it was 7.4.

Absent a membrane, the precipitation procedure of a mixture of DNA and binding buffer failed. The isolation is attributable to the membrane modification at selected pH conditions, and not to a precipitation reaction.

The invention claimed is:

1. A method for purifying nucleic acids present in a raw material, the method comprising:
providing a flow-permeable membrane or matrix having a surface functionalized with deprotonable groups that are bound to polymer chains, the polymer chains having a first end that is fixed to the membrane or matrix and a second end that is displaceable away from the membrane or matrix;
permeating the membrane or matrix with a solution comprising the raw material and a binding buffer, wherein the pH value of the solution is less than or about the same as the pK value of the surface of the membrane or matrix such that the polymer chains rest against the membrane or matrix to cause the nucleic acids in the solution to become selectively bound to the surface of the membrane or matrix; and
eluting the nucleic acids bound to the surface of the membrane or matrix by permeating the membrane or matrix with an elution buffer having a pH value that is greater than the pK value of the surface of the membrane such that the second ends of the polymer chains are displaced away from the membrane or matrix.

2. The method as claimed in claim 1, wherein the solution comprising the raw material and the binding buffer further comprises a precipitant in a concentration less than will cause the nucleic acids to precipitate.

3. The method as claimed in claim 2, wherein the solution comprising the raw material and the binding buffer contains PEG in a concentration less than 10%.

4. The method as claimed in claim 2, wherein the ionic concentration of the elution buffer is less than 500 mM.

5. The method as claimed in claim 2, wherein the solution comprising the raw material and binding buffer is vacuum aspirated through the membrane or matrix.

6. The method as claimed in claim 2, wherein the eluting step is carried out at room temperature.

7. The method as claimed in claim 2, wherein the raw material is subjected to pre-purification in order to remove coarse cell debris and the like.

8. The method as claimed in claim 2, wherein the raw material is a clarified cell lysate.

9. The method as claimed in claim 1, wherein the ionic concentration of the elution buffer is less than 500 mM.

10. The method as claimed in claim 1, wherein the solution comprising the raw material and binding buffer is vacuum aspirated through the membrane or matrix.

11. The method as claimed in claim 1, wherein the eluting step is carried out at room temperature.

12. The method as claimed in claim 1, wherein the raw material is subjected to pre-purification in order to remove coarse cell debris and the like.

13. The method as claimed in claim 1, wherein the raw material is a clarified cell lysate.

14. The method as claimed in claim 1, wherein the solution comprising the raw material and the binding buffer contains PEG in a concentration less than 10%.

15. The method as claimed in claim 1, wherein the polymer chains are formed of polyacrylic acid.

16. The method as claimed in claim 1, wherein the deprotonable groups bound to the polymer chains are sulfonic acid, carboxylic acid and/or phosphoric acid groups.

* * * * *